US011224358B2

(12) United States Patent
Johnson et al.

(10) Patent No.: US 11,224,358 B2
(45) Date of Patent: Jan. 18, 2022

(54) SMART MONITORING SAFETY AND QUALITY OF LIFE SYSTEM USING SENSORS

(71) Applicant: CareView Communications, Inc., Lewisville, TX (US)

(72) Inventors: Steven Gail Johnson, Highland Village, TX (US); Derek del Carpio, Corinth, TX (US)

(73) Assignee: CareView Communications, Inc., Lewisville, TX (US)

( * ) Notice: Subject to any disclaimer, the term of this patent is extended or adjusted under 35 U.S.C. 154(b) by 155 days.

(21) Appl. No.: 16/451,164

(22) Filed: Jun. 25, 2019

(65) Prior Publication Data

US 2019/0388011 A1    Dec. 26, 2019

Related U.S. Application Data

(60) Provisional application No. 62/689,281, filed on Jun. 25, 2018.

(51) Int. Cl.
*A61B 5/11* (2006.01)
*G16H 40/63* (2018.01)
*A61B 5/00* (2006.01)

(52) U.S. Cl.
CPC ............ *A61B 5/1118* (2013.01); *A61B 5/002* (2013.01); *A61B 5/1123* (2013.01); *A61B 5/6889* (2013.01); *A61B 5/7246* (2013.01); *G16H 40/63* (2018.01); *A61B 2503/08* (2013.01); *A61B 2505/07* (2013.01)

(58) Field of Classification Search
CPC . A61B 2503/07; A61B 2503/08; A61B 5/002; A61B 5/1118; A61B 5/1123; A61B 5/6889; A61B 5/7246; G16H 40/63; G16H 50/30; G16H 10/60; G16H 1515/00
See application file for complete search history.

(56) References Cited

U.S. PATENT DOCUMENTS

| 9,866,507 | B2* | 1/2018 | Frenkel | H04L 67/306 |
| 2013/0096404 | A1* | 4/2013 | Colman | A61B 5/113 |
| | | | | 600/324 |
| 2015/0156567 | A1* | 6/2015 | Oliver | G08B 21/24 |
| | | | | 340/870.07 |

(Continued)

*Primary Examiner* — Sean P Dougherty
*Assistant Examiner* — Alexander H Connor
(74) *Attorney, Agent, or Firm* — Meister Seelig & Fein LLP; Seth H. Ostrow, Esq.

(57) ABSTRACT

A smart monitoring system comprising a plurality of sensor devices within a home or facility, at least one of the plurality of sensor devices comprising sensor elements configured to detect activity of an individual in the home or facility, and a computing device configured to receive activity signals from the plurality of sensor devices associated with the individual, parse the activity signals into scoring components including a sleep score, a motion score, and an event score, compute a current scoring of the individual based on the scoring components, compare the current scoring of the individual to historic scoring and peer scoring, generate a quality of life score for the individual based on the based on the comparison, and process a clinical analysis of the individual based on the quality of life score, the clinical analysis including graphical representations of the quality of life score and the scoring components.

20 Claims, 7 Drawing Sheets

(56) References Cited

U.S. PATENT DOCUMENTS

2017/0172463 A1* 6/2017 Papadopoulos .... A61B 5/02427
2017/0301208 A1* 10/2017 Mytelka ............. G08B 21/0469
2018/0122209 A1* 5/2018 Jefferson ............. A61B 5/0015

* cited by examiner

Quality of Life

| | Self Current | Self Current vs Last Month | Self Current vs Peers |
|---|---|---|---|
| Sleep Score | 20% | 10% | 10% |
| Motion Score | 10% | 10% | 10% |
| Event Score | 10% | 10% | 10% |
| Panic | -10 points per incident | | |
| Score | 100% | | |

FIG. 5

Date Range: 01/01/2018 through 03/31/2018

Quality of Life

Sleep Quality

Panic Button

Triggers

Incidents

01-13-2018 - Panic Button Pressed
01-16-2018 - No Movement for 24 Hours
01-25-2018 - Panic Button Pressed
02-14-2018 - No Movement for 24 Hours

SMART MONITORING SAFETY AND QUALITY OF LIFE SYSTEM USING SENSORS

CROSS-REFERENCE TO RELATED APPLICATIONS

The present application is related to the following patents and applications, which are assigned to the assignee of the present invention:
a. U.S. Pat. No. 7,477,285, filed Dec. 12, 2003, entitled "Non-intrusive data transmission network for use in an enterprise facility and method for implementing,"
b. U.S. Pat. No. 8,471,899, filed Oct. 27, 2009, entitled "System and method for documenting patient procedures,"
c. U.S. Pat. No. 8,675,059, filed Jul. 29, 2010, entitled "System and method for using a video monitoring system to prevent and manage decubitus ulcers in patients,"
d. U.S. Pat. No. 8,676,603, filed Jun. 21, 2013, entitled "System and method for documenting patient procedures,"
e. U.S. Pat. No. 9,041,810, filed Jul. 1, 2014, entitled "System and method for predicting patient falls,"
f. U.S. application Ser. No. 12/151,452, filed May 6, 2008, entitled "System and method for predicting patient falls,"
g. U.S. application Ser. No. 14/039,931, filed Sep. 27, 2013, entitled "System and method for monitoring a fall state of a patient while minimizing false alarms,"
h. U.S. application Ser. No. 13/429,101, filed Mar. 23, 2012, entitled "Noise Correcting Patient Fall Risk State System and Method for Predicting Patient Falls,"
i. U.S. application Ser. No. 13/714,587, filed Dec. 14, 2012, entitled "Electronic Patient Sitter Management System and Method for Implementing,"
j. U.S. application Ser. No. 14/158,016, filed Jan. 17, 2014, entitled "Patient video monitoring systems and methods having detection algorithm recovery from changes in illumination,"
k. U.S. application Ser. No. 14/188,396, filed Feb. 24, 2014, entitled "System and method for using a video monitoring system to prevent and manage decubitus ulcers in patients,"
l. U.S. application Ser. No. 14/213,163, filed Mar. 13, 2014, entitled "System and method for documenting patient procedures,"
m. U.S. application Ser. No. 14/209,726, filed Mar. 14, 2014, entitled "Systems and methods for dynamically identifying a patient support surface and patient monitoring,"
n. U.S. application Ser. No. 14/710,009, filed May 12, 2015, entitled "Electronic Patient Sitter Management System and Method for Implementing,"
o. U.S. application Ser. No. 15/332,283, filed Oct. 24, 2016, filed Oct. 22, 2015, entitled "PATIENT VIDEO MONITORING SYSTEMS AND METHODS FOR THERMAL DETECTION OF LIQUIDS," and
p. U.S. application Ser. No. 15/364,872, filed Nov. 20, 2016, entitled "SYSTEM AND METHOD FOR PREDICTING PATIENT FALLS," the disclosure of which are hereby incorporated by reference in their entirety.
This application claims the priority of U.S. Provisional Application No. 62/689,281, filed on Jun. 25, 2018, entitled "SMART MONITORING SAFETY SYSTEM USING SENSORS," the disclosure of which is hereby incorporated by reference in its entirety.

The above identified patents and applications are incorporated by reference herein in their entirety.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

Field of the Invention

This application generally relates to a smart monitoring system, and in particular, a plurality of devices, including intelligent-sensing network-connected devices, that communicate with each other and/or with a central server or a cloud-computing system to provide safety and improved quality of life.

Description of the Related Art

Healthcare monitoring suffers from the disadvantage of requiring staff if the monitoring is to be in the form of direct observation. A closed-circuit visual and/or audio feed monitor requires a caregiver to be vigilant about monitoring the feed to sense the problem in the distant room. Thus, the trend in patient monitoring has been toward the use of electrical devices to signal changes in a patient's circumstance to a caregiver who might be located either nearby or remotely at a central monitoring facility, such as a nurse's station. An automated hospital care system improves quality of care and reduces chance for errors.

Patients are increasingly being monitored, cared for, and/or treated outside a conventional hospital environment. For example, home healthcare is growing trend wherein patients are monitored and treated from their homes. Home healthcare is generally less expensive and also frees up hospital resources allowing the hospital to focus on patients with more critical needs. However, among other worries, family members and health care professionals are concerned about patient forgetfulness (e.g., not remembering to take medication), confusion (e.g., taking an incorrect dosage of medication), wellness monitoring (e.g., making sure the patient has not become incapacitated), and ability to summon help (e.g., sending an alarm in an emergency). Thus, there exists a need for a smart monitoring system that would address and solve the above-described problems to improve safety and quality of life.

SUMMARY OF THE INVENTION

The present application discloses a smart monitoring system comprising a plurality of sensor devices within a home or facility, at least one of the plurality of sensor devices comprising sensor elements configured to detect activity of an individual in the home or facility, and a computing device configured to receive activity signals from the plurality of sensor devices associated with the individual from the home or facility, parse the activity signals into scoring components by correlating the plurality of sensor devices to the scoring components, the scoring components including a sleep score, a motion score, and an event score, compute a current scoring of the individual based on the scoring components, compare the current scoring of the individual to historic scoring and peer scoring, generate a quality of life score for the individual based on the based on the comparison, and process a clinical analysis of the individual based on the quality of life score, the clinical analysis including graphical representations of the quality of life score and the scoring components.

The activity signals may include utilization of appliances and motion in given rooms or areas. The computer device may be further configured to interpret activities based on type and location of the plurality of sensor devices. The activities may include walking, sleeping, eating, exercise, and bathroom activities. The current scoring of the individual may comprise a total of current scores of the scoring components. In one embodiment, the historic scoring includes a comparison of the scoring components with a historical set of scoring components associated with the individual. The peer scoring may include a comparison of the scoring components with scoring components of other individuals. The other individuals may be selected from a subset of a population according to one or more of age, race, sex, and location.

The quality of life score may comprise a weighted average or sum of the scoring components of the current scoring, the historic scoring, and the peer scoring. The computing device may further determine incidents of panic and decreases the quality of life score based on the incidents of panic. The computing device may further determine trends associated with health and safety conditions from the activity signals. The trends can include behaviors in eating, sleeping, mobility and hygiene.

In certain embodiments, the appliances and fixtures are selected from the group consisting of a toilet, a door, a window, a refrigerator, a television remote, and a medicine cabinet. The computing device may receive activity signals from a sensor device coupled to a handle of the toilet, and determines flushing of the toilet based on the activity signals from the sensor device coupled to the handle of the toilet. Another embodiment may include the computing device receiving activity signals from a sensor device coupled to the door, and determining an opening or closing of the door based on the activity signals from the sensor device coupled to the door. Yet another embodiment includes the computing device receiving activity signals from a sensor device coupled to the window, and determining an opening or closing of the window based on the activity signals from the sensor device coupled to the window.

The computing device may also receive activity signals from a sensor device coupled to the refrigerator, and determine an opening or closing of the refrigerator based on the activity signals from the sensor device coupled to the refrigerator. The computing device is also able to receive activity signals from a sensor device coupled to the television remote, and determine watching of a television based on the activity signals from the sensor device coupled to the television remote. Additionally, the computing device can be configured to receive activity signals from a sensor device coupled to the medicine cabinet, and determine an individual taking medicine based on the activity signals from the sensor device coupled to the medicine cabinet.

BRIEF DESCRIPTION OF THE DRAWINGS

The invention is illustrated in the figures of the accompanying drawings which are meant to be exemplary and not limiting, in which like references are intended to refer to like or corresponding parts, and in which:

FIG. 5 illustrates scoring components for quality of life assessment according to an embodiment of the present invention.

DETAILED DESCRIPTION OF THE INVENTION

Subject matter will now be described more fully hereinafter with reference to the accompanying drawings, which form a part hereof, and which show, by way of illustration, exemplary embodiments in which the invention may be practiced. Subject matter may, however, be embodied in a variety of different forms and, therefore, covered or claimed subject matter is intended to be construed as not being limited to any example embodiments set forth herein; example embodiments are provided merely to be illustrative. It is to be understood that other embodiments may be utilized and structural changes may be made without departing from the scope of the present invention. Likewise, a reasonably broad scope for claimed or covered subject matter is intended. Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of exemplary embodiments in whole or in part. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

The present disclosure relates to facilitating management of healthcare, safety, and well-being, including monitoring and assessing the quality of patient care, and provides data, reports, analytics, etc. related thereto. The invention provides embodiments of systems and methods which facilitate management of health care at home or provided by a facility, e.g., assisted living or long-term care homes. Embodiments of the present disclosure generally relate to a plurality of devices, including intelligent-sensing network-connected devices, that communicate with each other and/or with a central server or a cloud-computing system for monitoring and assessing safety and quality of life of patients or cared-for individuals. In particular, a smart monitoring environment is disclosed that increases awareness around an individual and improves safety by leveraging multiple sensors that work in conjunction to help identify and describe information about the individual, specifically with regards to safety and quality of life.

Figure 1:
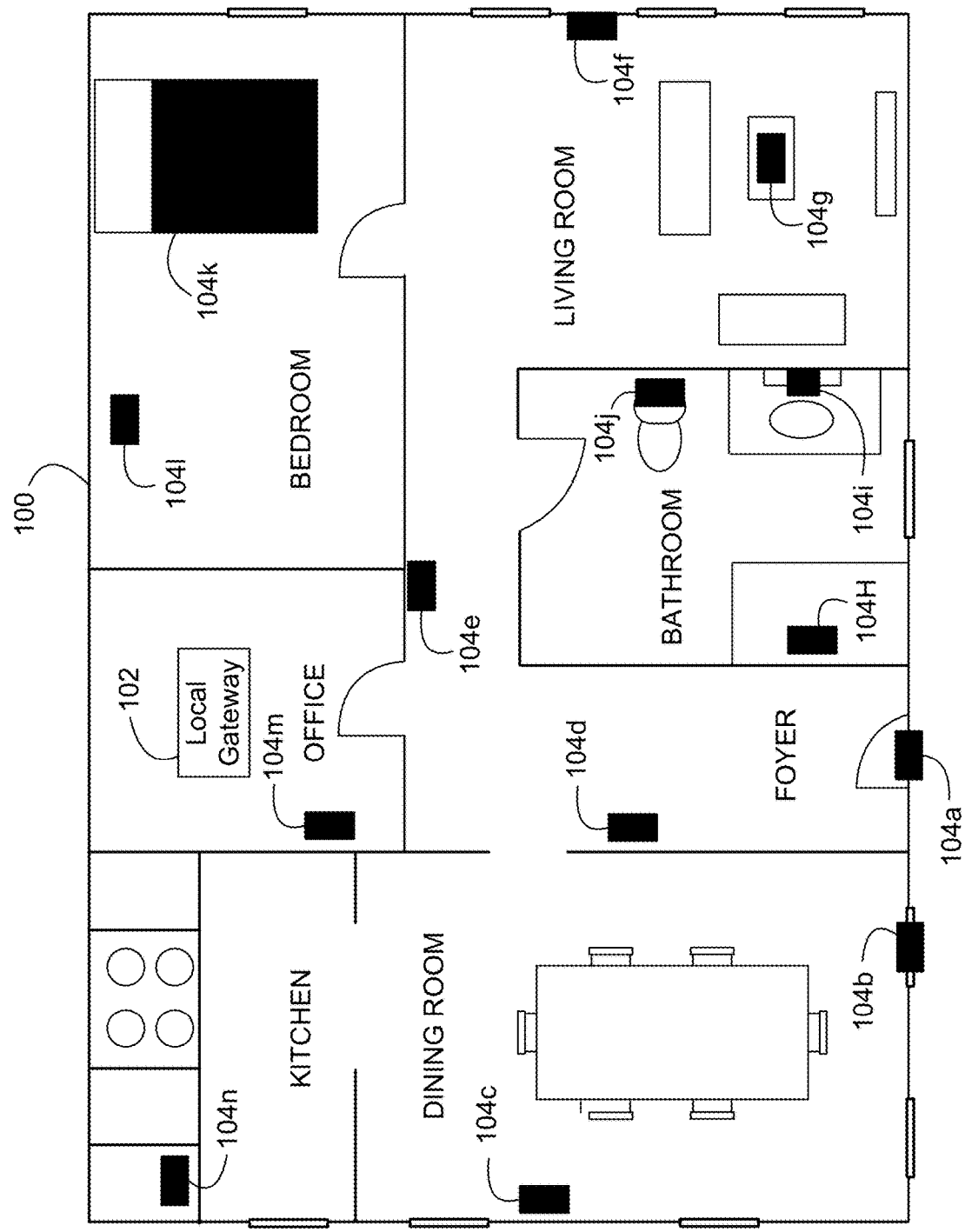
FIG. 1 illustrates a smart monitoring environment according to an embodiment of the present invention.

FIG. 1 illustrates an example of a smart monitoring environment according to an embodiment of the present invention. The depicted smart monitoring environment includes a structure 100, which can include, e.g., a house, office building, assisted living and/or long-term care facility, mobile home, or any other dwelling environment. The smart monitoring environment of FIG. 1 includes a plurality of sensor devices 104a-104n comprised of intelligent-sensing network-connected devices, that can integrate seamlessly with each other and/or with a central server or a cloud-computing system. The depicted structure 100 includes a plurality of rooms where the sensor devices 104a-104n can be mounted on, integrated with and/or supported by a wall, floor, or ceiling.

In some embodiments, sensor devices 104a-104n may comprise room motion sensors, individual safety sensors, individual location sensors, appliance/fixture sensors, and any combination thereof. Room motion sensors may comprise devices that connect a passive infrared sensor (PIR) to a component able to communicate with local gateway 102 via wireless communication technology such as Bluetooth low energy (LE), IEEE 802.11, or other means of data transmission. In some embodiments, a plurality of local gateways may be deployed to improve coverage and performance in receiving signals from the plurality of sensor devices 104a-104n. For example, a local gateway may be deployed on each floor of a house. A sensor device including a room motion sensor may look for motion in a room and report measurements to local gateway 102. For example, sensor devices 104c, 104d, 104f, 104e, 104h, 104l, and 104m, may comprise at least room motion sensors for determining occupancy of given rooms or areas within structure 100. Positioning of sensor devices can be mapped to a blueprint of a room, floor, dwelling, or building to increase accuracy of information and help interested parties understand where motion is occurring. In one embodiment, the sensors devices may be tagged, assigned, or programmed in accordance to their physical locations or proximity to given objects, such as beds, appliances, fixtures, etc.

A sensor device including individual safety sensors may comprise devices including one or more push buttons (e.g., a panic button) connected to a beacon component able to communicate with local gateway 102 via wireless communication technology. A button of the individual safety sensor may capture and immediately notify interested parties when pushed by the individual, of an emergency or when in need of immediate help. According to one embodiment, during button press of the individual safety sensors, a light-emitting diode (LED) light may illuminate in lock step with button press for comfort feedback. Alternatively, the LED light may blink (as opposed to a steady light) for power conservation and better visual feedback. Blinking of the LED light may further avoid simultaneous LED light and radio power consumption from communication with local gateway 102 by alternating intervals between wireless transmissions and LED light blinking.

Upon button press, a beacon signal may be communicated to local gateway 102. The beacon signal may include button press duration to convey urgency and/or uniquely identify events or devices. Beacon signals may be received by multiple local gateways to improve detection rate. A central server may receive the beacon signals and de-duplicate them from multiple gateways before analysis. An event counter (e.g., number of unique button presses) and button press duration may be used algorithmically by the server to interpret the beacon signals. The central server may include data analytics or artificial intelligence that can be used to interpret button press urgency from the event counter and button press duration. For instance, a brief button press could be interpreted as an accidental button press while repeated rapid or lengthy button presses may indicate urgency and an emergency.

Appliance/fixture sensors may comprise accelerometers connected to a component able to communicate with the local gateway 102 via wireless communication technology. Accelerometer motion detected by the appliance/fixture sensors can indicate certain events. For example, sensor device 104j may be an appliance/fixture sensor mounted on the toilet handle to detect movement, where movement corresponds to an individual flushing the toilet. Other examples of appliance/fixture sensors may include: sensor device 104a adhered to a door can indicate when a door has been opened, closed, or broken; sensor device 104b adhered to a window can indicate when a window has been opened, closed, or broken; sensor device 104n adhered to a kitchen appliance, such as, a refrigerator, can indicate when the refrigerator has been opened and closed; sensor device 104g adhered to an entertainment device, such as, a television remote, can indicate usage/watching of television; and sensor device 104i adhered to a medicine cabinet can indicate an individual taking medicine.

In certain embodiments, the smart monitoring environment may further include near-field sensor devices that may uniquely identify some action with a person (family, care-giver, individual) or object (medication, asset). The near-field sensor devices may detect signals from wireless transmitter devices, such as RFID (radio-frequency identification), worn by or attached to people or objects. For example, a near-field sensor device may notify that a care-giver entered and left the room, or that an individual took medication at a given time. A near-field sensor device may comprise a device that connects a near-field communication (NFC) sensor to a component able to communicate with the local gateway 102 via wireless communication technology.

According to another embodiment, the smart monitoring environment may further include individual motion sensors comprised of a device that connects an accelerometer to a component able to communicate with the local gateway 102 via wireless communication technology. The individual motion sensor may monitor the individual's orientation and motion to detect events. For example, the individual motion sensors can detect a possible fall event from values corresponding to measurements of movement matching one or more patterns. Such a sensor can be contained in a water-proof enclosure and, for example, adhered to the back of the individual's collar or similar fixed apparel on the individual whereby there should be little error introduced by motion that is not caused by movement of the body.

Additional types of sensors and actuators can include, but are not limited to: cameras, thermal imaging, bed sensors (e.g., 104k), microphone, speaker, touch screen display, and thermometer/thermostat that may be applied, attached, or integrated with to stoves and/or ovens, washers, dryers, indoor or outdoor lighting, stereos, intercom systems, gated entries, garage-door openers, floor fans, ceiling fans, wall air conditioners, pool heaters, irrigation systems, security systems, safes, and so forth. Individual location sensors may comprise devices that identify a current location of an individual and communicates with local gateway 102 via wireless communication technology. For the purpose of improving accuracy, the system can rely on the position of any fixed-location component, such as the local gateway 102 or a room motion sensor. Any of the sensors described herewith may exist independently or be combined in a single enclosure, such as combining an individual location sensor with an individual motion sensor and/or an individual safety sensor.

It should be appreciated that the smart monitoring environment may further include areas outside the home, such as curtilage, the yard, and other nearby land. Further, the smart monitoring environment can control and/or be coupled to devices and sensors outside of the actual structure 100. Several devices in the smart monitoring environment need not physically be within the structure 100. For example, a device controlling an outdoor lighting system or gated entry system can be located outside of the structure 100.

By leveraging multiple sensors, individuals can be monitored within structure 100 for their safety and to improve their quality of life. In addition to containing processing and sensing capabilities, each of the sensor devices are capable of data communications and information sharing with any other of the sensor devices, as well as to any central server or cloud-computing system or any other device. Family and/or caregivers can review information that is collected to determine if the individual is behaving normally or not. As an example, if the individual typically leaves their room three hours per day, but suddenly shows leaving for only one hour per day then those connected to the individual can be notified. Events, such as falls or other potentially life-threatening events, may also be recorded and used to notify families and/or caregivers. Families and/or caregivers can log into a web portal or mobile application to review observed information, trends and notifications generated from the sensor devices. This information may be presented in the form of graphs showing trends, as well as a simple numerical value or score that identifies risk to safety and deviation from normal observations.

Figure 2:
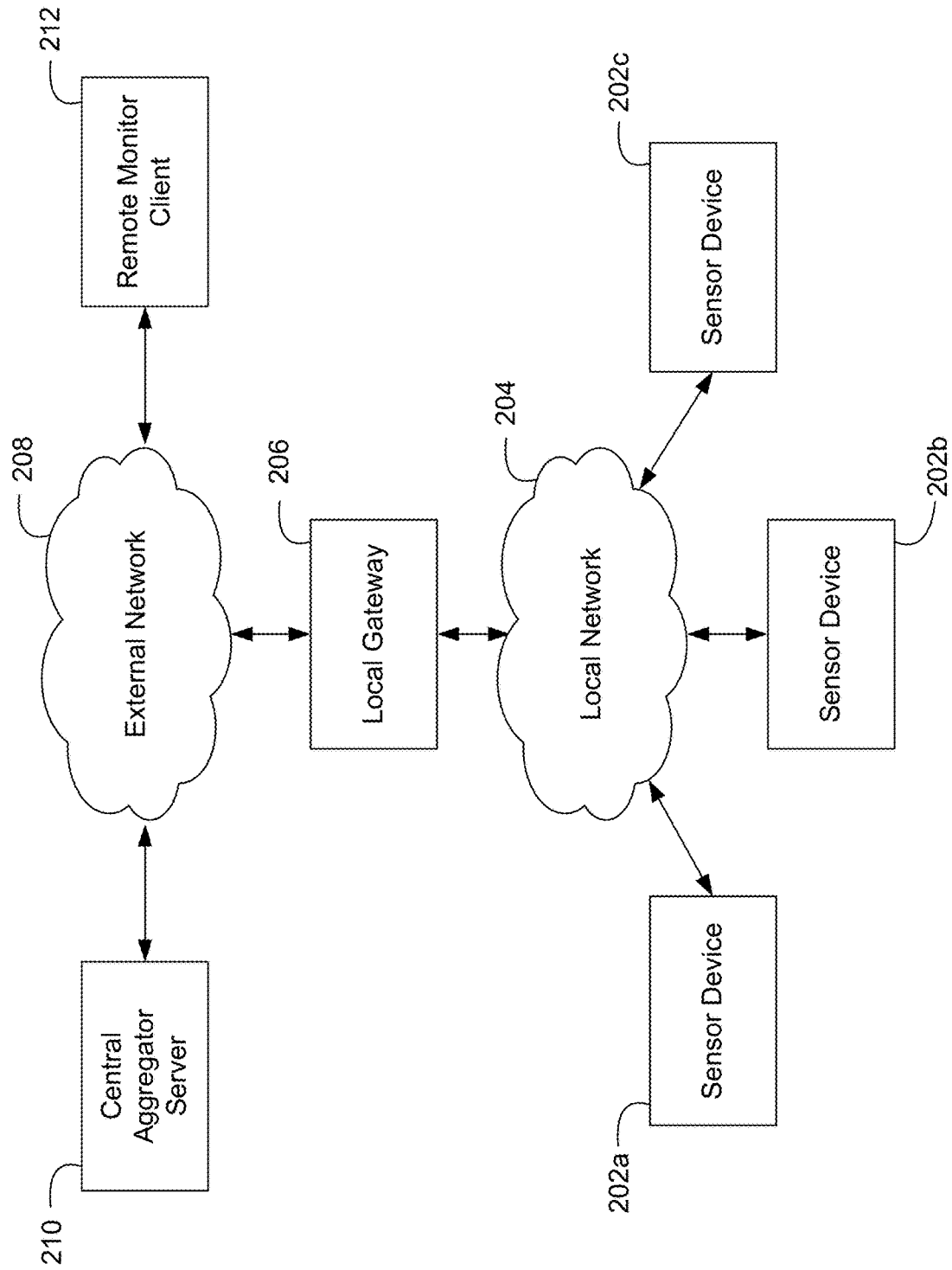
FIG. 2 illustrates a networked system according to an embodiment of the present invention.

FIG. 2 presents a networked system including a plurality of devices from a smart monitoring environment such as the one illustrated in FIG. 1. Sensor devices 202*a*, 202*b*, and 202*c* and local gateway 206 may be installed within a home or facility to monitor elderly or disabled individuals living in the home or facility. Sensor devices 202*a*, 202*b*, and 202*c* can communicate with each other and with local gateway 206 through local network 204 wirelessly via Bluetooth LE, IEEE 802.11, or other transmission methods. Local gateway 206 may comprise a device at the individual's residence or room that collects information from the sensor devices. Local gateway 206 may include or may be communicatively connected to processor and memory devices that may be used to access, setup, or program sensor devices 202*a*, 202*b*, and 202*c*. The collected information may be communicated through the external network 208 via Ethernet, 802.11 wireless, or other means of transmission, from local gateway 206 to central aggregator server (or cloud-computing system) 210 for storage and processing.

External network 208 may be any suitable type of network allowing transport of data communications across thereof. The external network 208 may couple devices so that communications may be exchanged, such as between servers and client devices or other types of devices, including between wireless devices coupled via a wireless network, for example. A network may also include mass storage, such as network attached storage (NAS), a storage area network (SAN), cloud computing and storage, or other forms of computer or machine readable media, for example. In one embodiment, the network may be the Internet, following known Internet protocols for data communication, or any other communication network, e.g., any local area network (LAN) or wide area network (WAN) connection, cellular network, wire-line type connections, wireless type connections, or any combination thereof. Communications and content stored and/or transmitted to and from client devices may be encrypted using, for example, the Advanced Encryption Standard (AES) with a 256-bit key size, or any other encryption standard known in the art.

The central aggregator server 210 may include data storage and means of data analysis that collates information from sensors 202*a*, 202*b*, and 202*c* gathered via local gateway 206. The central aggregator server 210 can be hosted at the facility or may exist as a cloud-based service. For example, central aggregator server 210 may comprise at least a special-purpose digital computing device including at least one or more central processing units and memory. The special-purpose digital computing device may also include one or more of mass storage devices, power supplies, wired or wireless network interfaces, input/output interfaces, and operating systems, such as Windows Server, Mac OS X, Unix, Linux, FreeBSD, or the like.

Central aggregator server 210 can generate data, statistics, and notifications from the collated information. Data from sensor devices 202*a*, 202*b*, and 202*c* may be analyzed, for example, in combination with rules-based inference engines and/or artificial intelligence and/or any suitable smart environment data. Sensor devices 202*a*, 202*b*, and 202*c* may be configured with unique identifiers, labels, or tags associated with certain rooms, zones, locations, or appliances. As such, sensor devices 202*a*, 202*b*, and 202*c* may be distinguishable to artificial intelligence/machine learning systems and users. Additionally, central aggregator server 210 may correlate the sensor devices 202*a*, 202*b*, and 202*c* with programmable rules and triggers based on the unique identifiers, labels, or tags (or rooms, zones, locations, or appliances). A machine learning system may use data from the sensor devices 202*a*, 202*b*, and 202*c* and correlate them to certain locations or objects for training and classification.

Central aggregator server 210 is operative to receive requests from remote monitor client 212 and process the requests to generate responses to the remote monitor client 212 across the external network 208. The central aggregator server 210 may provide analysis, recording of data, alerts, and messages associated with activity from sensor devices 202*a*, 202*b*, and 202*c* to the remote monitor client 212. Data generated by central aggregator server 210 may be accessed by a remote monitor client 212 using a web portal and/or mobile application. Remote monitor client 212 may be used by families and/or caregivers to review server/artificial intelligence-observed information from the sensor devices, trends, and notifications generated based on information from the sensor devices useful for monitoring an observed individual, such as, a patient or elderly person, to ensure their well-being and safety. For example, family members can check on the individual from their mobile phone, and receive alerts when certain patterns or conditions occur.

The central aggregator server 210 may be associated with a manufacturer, support entity, or service provider associated with the network-connected sensor devices. For one embodiment, a user may be able to contact local law enforcement and other emergency or security personnel as well as contact customer support at a service provider using one of the network-connected sensor devices itself rather than needing to use other communication means such as a telephone or Internet-connected computer. Additionally, central aggregator server 210 may also contact or send a signal to one of sensor devices 202*a*, 202*b*, 202*c*, or a communication device upon triggering programmable rules or triggers. In one embodiment, a programmable rule or trigger may be based on a monitored individual's quality of life score. According to an alternative embodiment, functionality of the central aggregator server 210 may be optionally replaced by the local gateway 206. Such a change effectively decentralizes the data so that local gateway 206 can host the data, present the web portal, and provide a means for a mobile application to communicate with.

Remote monitor client 212 may comprise computing devices (e.g., desktop computers, television set top boxes, terminals, laptops, personal digital assistants (PDA), cell phones, smartphones, tablet computers, e-book readers, smart watches and wearable devices, or any computing device having a central processing unit and memory unit capable of connecting to a network). Client devices may also comprise a graphical user interface (GUI) or a browser application provided on a display (e.g., monitor screen, LCD or LED display, projector, etc.). A client device may also include or execute an application to communicate content, such as, for example, textual content, multimedia content, or the like. A client device may include or execute a variety of operating systems, including a personal computer operating system, such as a Windows, Mac OS or Linux, or a mobile operating system, such as iOS, Android, or Windows Mobile, or the like.

Figure 3:
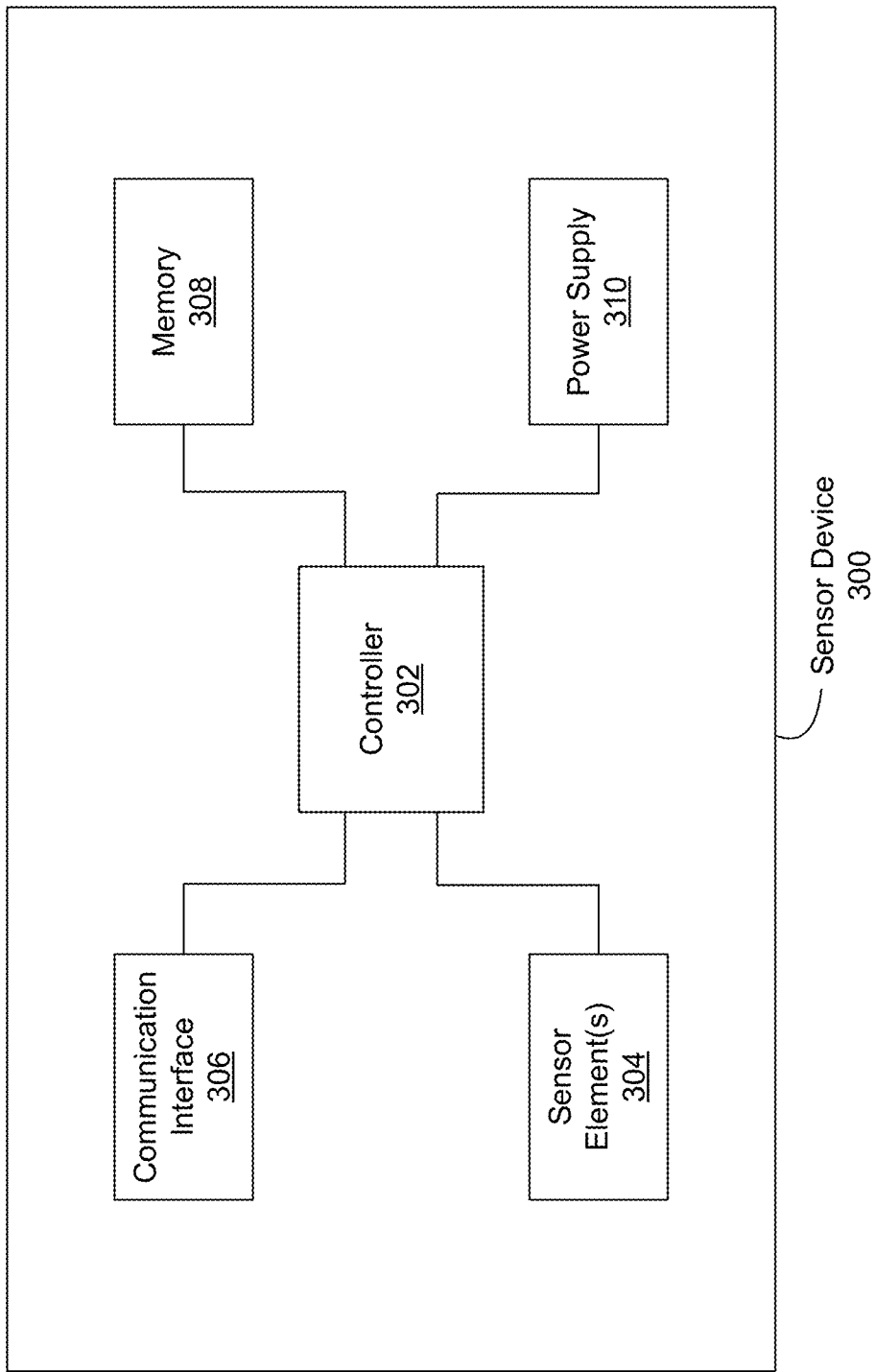
FIG. 3 illustrates a schematic overview of a sensor device according to an embodiment of the present invention.

FIG. 3 presents a schematic overview of a sensor device 300 according to an embodiment of the present invention. Sensor device 300 comprises sensor element(s) 304. According to one embodiment, the sensor device 300 may be an accelerometer-based movement sensor device. For example, sensor 300 may include sensor element(s) 304 comprising a movement sensor element containing an accelerometer and associated movement detection circuiting. As discussed above, the sensor device 300 may contain additional sensors of a different or second type in one or more embodiments. Such second type of sensors may be motion sensors, on-person worn sensors or other sensors known in the art. Such second type sensors may be dedicated sensors used for detecting a specific action that the sensor was designed to detect.

The sensor device 300 further comprises a controller 302, which may be implemented as one or more processors (CPU) or programmable logic circuits (PLC), which is connected to or comprises a memory 308. The memory may be implemented using any commonly known technology for electronic device memories such as read-only memory (ROM), random-access memory (RAM), static RAM (SRAM), dynamic RAM (DRAM), complementary metal-oxide-semiconductor (CMOS), flash memory, synchronous dynamic random-access memory (SDRAM), double data rate (DDR) SDRAM, or some other memory technology. The memory 308 is configured to store a definition of certain patterns to be detected. The sensor device 300 also comprises a communication interface 306. The communication interface may be a wireless radio frequency interface such as a Bluetooth or a IEEE 802.11 standard link. The communication interface 306 may also be a wired interface.

The controller 302 is configured to receive a sensing signal from the sensor element(s) 304 and to compare the signal to the definition of the patterns stored in the memory 308. If the signal matches the pattern, an event is detected. In response to a detected pattern, the controller 302 may be configured to activate the communication interface 306 and transmit a detection signal to one or more local gateways. Wireless communication transmissions from a sensor device 300 may also be increased to improve detection. For example, a sensor device may start at a lower rate for battery conservation and increased gradually or immediately to improve chances of detection and reduce time of detection.

The sensor device 300 may be powered by a power supply 310, such as a battery, a solar cell or other power supply. In certain embodiments, a sensor device may increase transmission power to improve detection during button presses (e.g., individual safety sensors). For example, the sensor device may start at a lower transmission power for battery conservation and gradually or immediately increase transmission power to improve a chance to detect transmissions from the sensor device. For example, a gradual increase may include a transmission at −20 dBm to −4 dBm and then to +4 dBm; and an immediate increase may include a transmission at −20 dBm to +4 dBm. Increases in transmission power during button presses may also be used to improve triangulation. For example, sensor devices may transmit a few signals at a variety of increasing power levels over time. Transmission power levels of sensor devices may be collected and used in analytics. Signals transmitted from sensor devices may also include event counters, tokens or identifiers to unique identify events from each sensor device at local gateways. The event counters, tokens or identifier may also help distinguish separate button presses (e.g., short press vs. long press, single-press vs. double-press, etc.).

Figure 4:
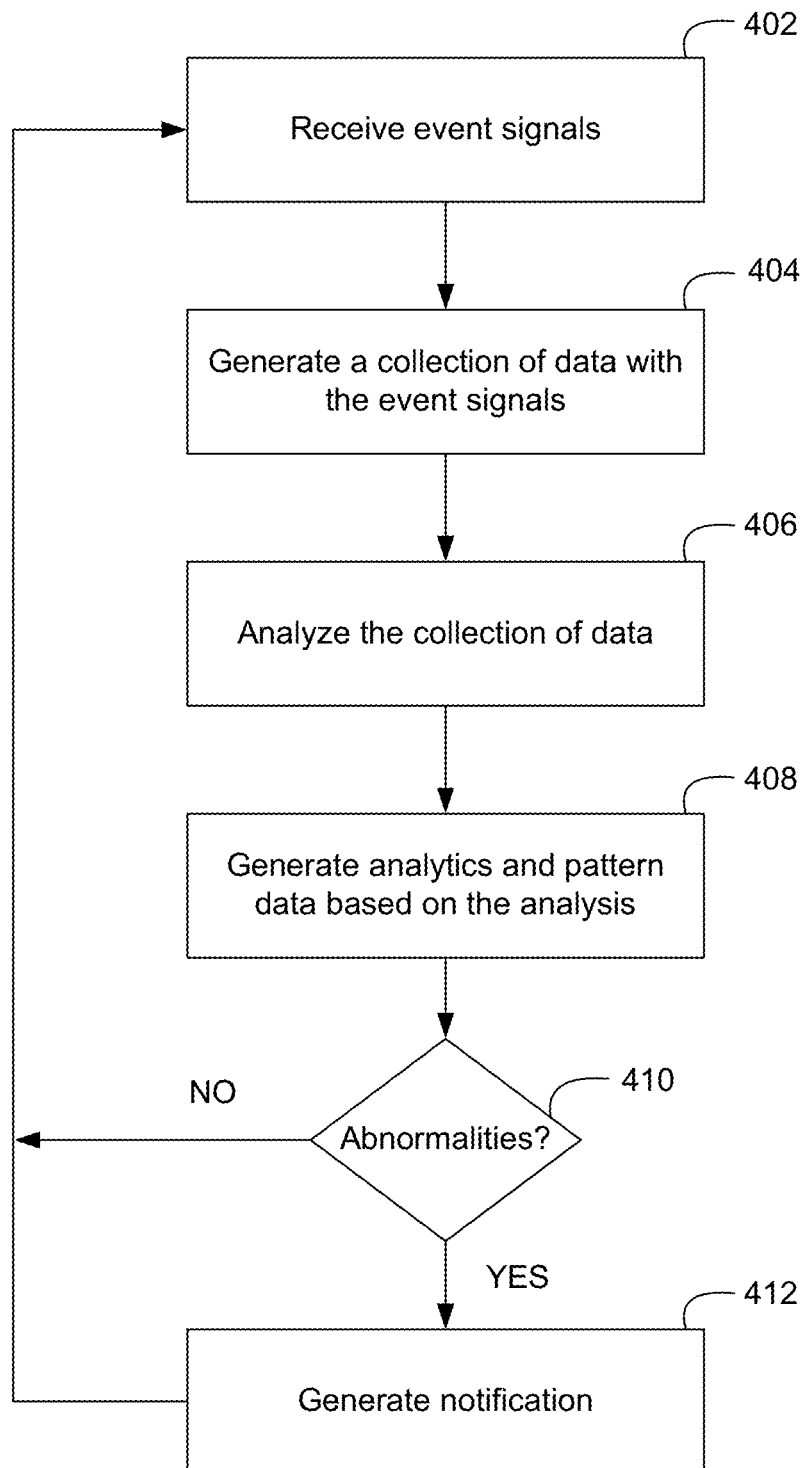
FIG. 4 illustrates a flowchart of a method for analyzing data received from devices of a smart monitoring environment according to an embodiment of the present invention.

FIG. 4 presents a flowchart of a method for analyzing data received from devices of a smart monitoring environment according to an embodiment of the present invention. One or more event signals are received by computing device such as a central aggregator server (or a local gateway in certain embodiments), step 402. The signals may be an aggregation of signals from sensor devices of a smart monitoring environment. A given signal received by the computing device may include data or indications of events associated with a specific function of a sensor device (e.g., motion, presence, location, usage, an alert, etc.).

A collection of data is generated with the event signals, step 404. The collection of data may be stored in a database. The collection of data including the event signals is analyzed by the computing device, step 406. The analysis may include artificial intelligence determining trends associated with health and safety conditions (e.g., quality of life) from the event signals such as behaviors in eating, sleeping, mobility, hygiene, to name a few. Data from the event signals may be correlated with the trends based on rules and/or artificial intelligence.

Analytics and pattern data are generated based the analysis of the collection of data, step 408. The analytics and pattern data may include logs, charts, graphs, and warnings based on the results of the analysis. The presence of abnormalities in the analytics and pattern data are determined by the computing device, step 410. The computing device generates a notification if there is a presence of abnormalities, such as warnings, in the analytics and pattern data, step 412.

A smart monitoring environment may utilize sensors to collect information about monitored individuals, specifically with regards to their quality of life. According to certain embodiments, the disclosed system may comprise a plurality of sensor devices in different homes or facilities, including intelligent-sensing network-connected devices, that communicate with a central server or a cloud-computing system that monitors and assesses quality of life among a plurality of patients or cared-for individuals. The system may aggregate and analyze sensor data from multiple homes or facilities to compute individual, community, and universal statistics.

Statistics may include averages and standard deviations for any detected activity on an individual basis, community basis, or universal basis.

The detected activity may correspond to one or more scoring components that can be used to calculate a quality of life score. Examples of scoring components may include scores that measure quality of sleep, motion, and other activities or attributes that affect quality of life. For example, a given individual's current levels of activity (e.g., current scores of a plurality of scoring components) may be used to compute a score (e.g., on a 0-100 scale) that shows the quality of life of the individual. The score may be compared against averages and standard deviations of the individual's level of activity over a period of time and/or compared to other monitored individuals of similar ages, demographic groups, etc.

As illustrated in FIG. 5, a set of scoring components may be computed against a weighted average to generate a cumulative score by using for example, a combination of current scores of scoring components (e.g., the last 24 hours), the scoring components with the current scores compared to a previous month, and the scoring components with the current scores compared to peers (e.g., an average over a given period). Sleep, motion, and event score components for a current score may be weighted at 20%, 10%, and 10%, respectively. While score components compared to the previous month and compared to peers may be weighted at 10% each. Combining all of the score components may give a maximum cumulative score of 100%. Incidents of panic (e.g., determined from activity signals or indicated by an individual via panic button press) may decrease or negatively affect the cumulative score by, for example, 10 points.

Each individual being monitored may be provided a means, such as devices including a panic button, to notify emergency response personnel, staff, caregivers, family members, etc., of the need for immediate intervention to keep the individuals safe or rescue them from a dangerous situation. Typical uses for a panic button include, but are not limited to, falls, sudden unexpected inability to meet personal care needs, and chest pain or dizziness indicating an emergency medical event. Panic button engagement may impact an individual's overall quality of life score.

Figure 6:
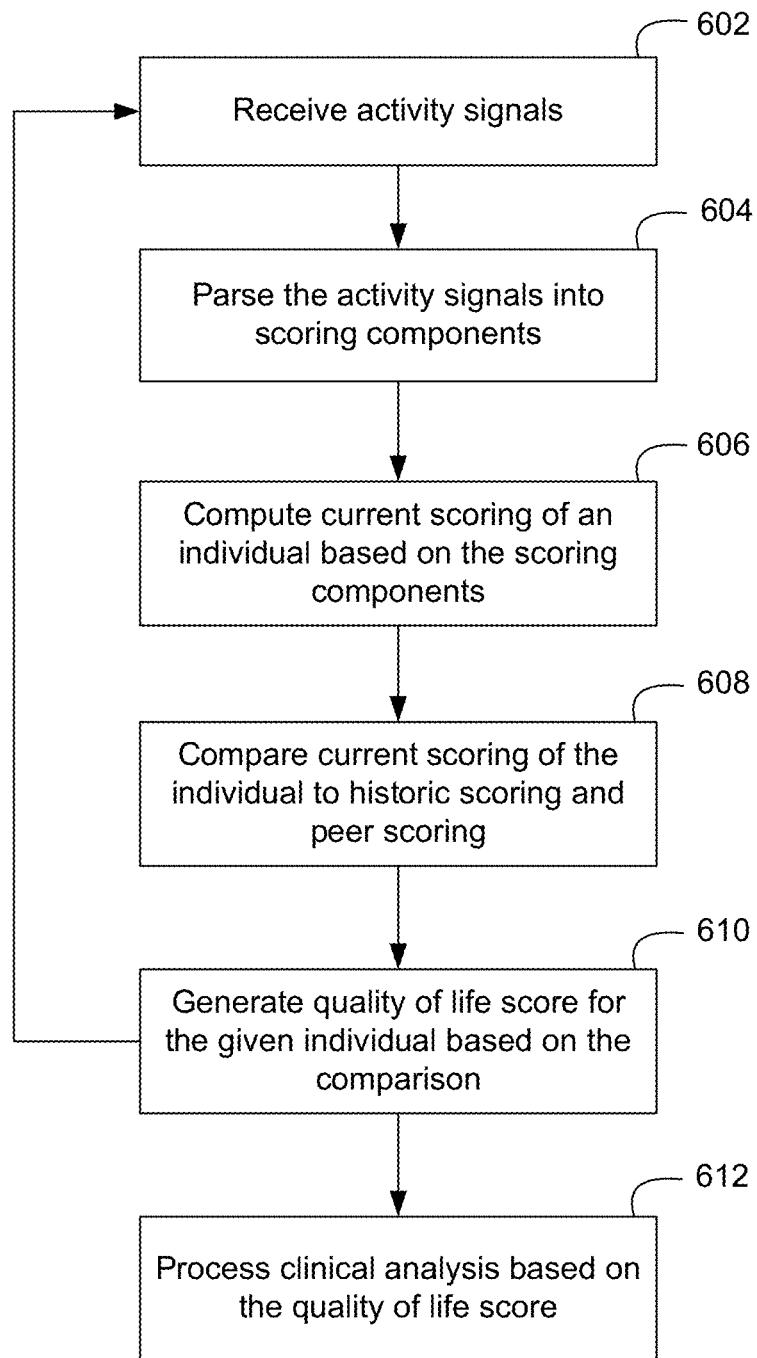
FIG. 6 illustrates a flowchart of a method for assessing quality of life according to an embodiment of the present invention.

FIG. 6 presents a flowchart of a method for assessing quality of life according to an embodiment of the present invention. A centralized server may be configured to monitor activities of individuals in homes and facilities. Activity from a given home or facility may be used to assess and monitor an individual's quality of life. An individual's quality of life may be measured in terms of general well-being that is experienced by the individual as perceived by sensors. Activity signals are received from a plurality of sensors associated with the individual from a given one of a plurality of homes and facilities, step 602. The activity signals may comprise detection by the plurality of sensors of utilization of various appliances, and/or motion in given rooms or areas of a home or facility. Activity signals may be correlated with daily activities performed by a monitored individual. Daily activities, such as sleeping, walking, eating, etc., may be used as criteria to determine the individual's quality of life.

The activity signals are parsed into scoring components, step 604. An individual's well-being may be represented by a collective of scoring components that are associated with activities or events related to the individual. Parsing the activity signals may include using the activity signals to interpret what an individual is doing on a daily basis that may or may not affect their overall well-being. The activity signals may also indicate various activities, such as walking, sleeping, eating, exercise, bathroom activities, etc., based on the kind of sensor device and location of the sensor the activity signals come from. Data corresponding to certain activities determined from the signals may be segmented into different scoring components. Activity signals from the sensor devices can be interpreted and used to assign scores to individual scoring components, such as a sleep score, a motion score, and an event score. As such, specific activity signals from the sensor devices may be correlated to different scoring components. For example, sensor devices in the bedroom may be correlated and contributed to the sleep score.

A current scoring of the individual is computed based on the scoring components, step 606. For example, the current scoring of the individual may comprise a total of current points assigned to a sleep score, a motion score, and an event score. The current scoring of the individual is compared to historic scoring and peer scoring, step 608. Comparing the current scoring to historic scoring may include comparing points of the scoring components with one or more historical sets of points of the scoring components that were assigned to the individual in the past, e.g., a month ago, and generating historic score components (e.g., sleep, motion, and event) based on the comparison. A comparison of the current scoring to peer scoring may include comparing the current scoring with current scoring of other individuals within the plurality of homes and facilities monitored by the centralized server and generating peer score components (e.g., sleep, motion, and event) based on the comparison. The other individuals may be a subset of a population selected according to age, race, sex, location, etc.

A quality of life score is generated for the individual based on the comparison, step 610. The quality of life score may be a weighted average or sum of the scoring components of the current scoring, the historic score components, and the peer score components. For example, the quality of life score may comprise an indicator having a numeric assignment on a 100-point scale by capturing weighted averages of critical indicators such as panic button use, abnormal triggers, and sleep quality and compares these combined weighted averages against markers, such as the individual's own historical or baseline scores and the score(s) of normally healthy peers. A clinical analysis of the individual is processed based on the quality of life score, step 612. The clinical analysis may include an overall assessment of the individual's well-being over time based on factors (or scoring components), such as panic button use, triggers, sleep quality, and the quality of life score. Processing of the clinical analysis may include generating graphical representations of the quality of life score and scoring components used to calculate the quality of life score.

Figure 7:
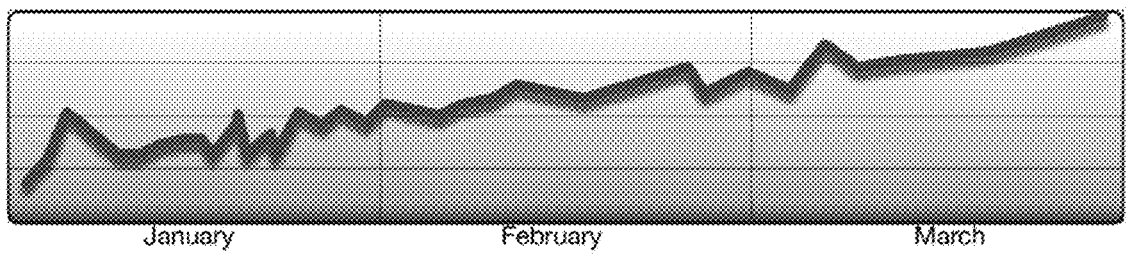
FIG. 7 presents an exemplary clinical analysis report according to an embodiment of the present invention.
Figure 7:
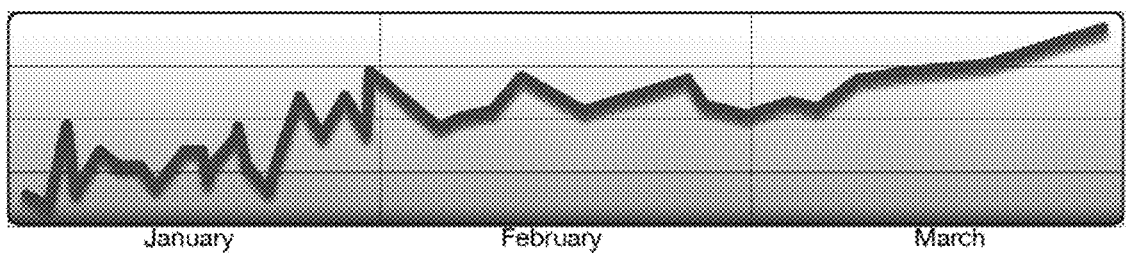
Figure 7:
Figure 7:
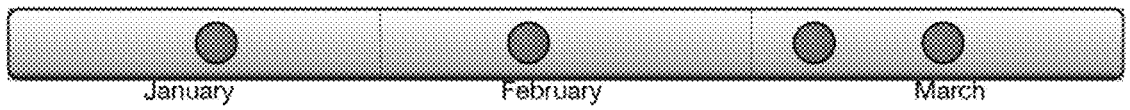

FIG. 7 presents an exemplary clinical analysis report for a given period according to an embodiment of the present invention. An individual may be provided a panic button or a means to notify staff of the need for immediate intervention to keep them safe or rescue them from a dangerous situation. Typical uses for the panic button include, but are not limited to, falls, sudden unexpected inability to meet personal care needs, and chest pain or dizziness indicating an emergency medical event. Referring to FIG. 7, during the report period, the individual may have engaged the panic button twice in January and twice in March for a total of four (4) times. The events in March were on the same day. Clinical staff should provide details regarding the reasons and outcomes of the panic button engagement. Panic button engagement can impact the individual's overall quality of life score.

Triggers may include behaviors registered by the disclosed system that fall outside typically normal behavior, such as panic button use, sleeping longer than 12 consecutive hours, sleeping past 8:00 a.m., and no routine medications taken in a 24-hour period. Triggers that are not captured as panic button engagements may further impact the individual's quality of life score (panic button engagements impact the quality of life score but are not counted as triggers to prevent duplication). As illustrated in FIG. 7, during this report period, the system registered four (4) trigger events. The details of these events may be listed on the clinical report (e.g., "incidents").

Sleep quality is another factor that may impact the individual's quality of life score. Sleep quality may be measured by the amount/length of uninterrupted sleep and the depth of sleep as captured by movement during sleep. A sleep quality index may be measured on a 100-point scale each day and averaged for measurement periods greater than daily, for example. According to FIG. 7, the individual may have experienced relatively poor sleep quality in the month of January but has experienced significant improvement through February and March yielding a score of 100 by the end of March.

Based on the above factors, the individual's quality of life indicator may indicate that the individual has experienced significant improvement in his/her quality of life score over the 3-month reporting period mirroring the improvement in sleep quality despite two (2) panic button engagements and two (2) additional triggers in March. In the illustrated example, the individual is enjoying a quality of life score that is a personal improvement and is aligned with the peer group.

FIGS. 1 through 7 are conceptual illustrations allowing for an explanation of the present invention. Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

It should be understood that various aspects of the embodiments of the present invention could be implemented in hardware, firmware, software, or combinations thereof. In such embodiments, the various components and/or steps would be implemented in hardware, firmware, and/or software to perform the functions of the present invention. That is, the same piece of hardware, firmware, or module of software could perform one or more of the illustrated blocks (e.g., components or steps). In software implementations, computer software (e.g., programs or other instructions) and/or data is stored on a machine readable medium as part of a computer program product, and is loaded into a computer system or other device or machine via a removable storage drive, hard drive, or communications interface. Computer programs (also called computer control logic or computer readable program code) are stored in a main and/or secondary memory, and executed by one or more processors (controllers, or the like) to cause the one or more processors to perform the functions of the invention as described herein. In this document, the terms "machine readable medium," "computer readable medium," "computer program medium," and "computer usable medium" are used to generally refer to media such as a RAM; a ROM; a removable storage unit (e.g., a magnetic or optical disc, flash memory device, or the like); a hard disk; or the like.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

What is claimed is:

1. A smart monitoring system, the system comprising:
a plurality of sensor devices within a home or facility, at least one of the plurality of sensor devices comprising at least one near-field sensor device, the at least one near-field sensor device configured to detect signals from one or more wireless transmitter devices coupled to an individual in the home or facility; and
a computing device configured to:
receive activity signals from the plurality of sensor devices, the activity signals including detected signals from the one or more wireless transmitter devices indicating a presence of the individual, and sensor data comprising values representative of measurements of movement associated with the presence of the individual and indicating usage of given ones of appliances and fixtures, wherein the usage of the given ones of the appliances and fixtures includes a button press and a press duration that is representative of urgency unique to the given ones of the appliances and fixtures;
parse the activity signals into scoring components by correlating the sensor data from the plurality of sensor devices to the scoring components, the scoring components including a sleep score, a motion score, and an event score;
compute a current scoring of the individual based on the scoring components;
compare the current scoring of the individual to historic scoring of the individual and peer scoring of the individual, the historic scoring and the peer scoring computed based on the scoring components;
generate a quality of life score for the individual based on the current scoring and using the comparison as a baseline;

process a clinical analysis of the individual based on the quality of life score, the clinical analysis including graphical representations of the quality of life score, the scoring components, and a trend associated with the individual's health based on the event signals, the trend including the indication of usage of the given ones of the appliances and fixtures corresponding to the presence of the individual and a distinctive press duration that indicates an emergency;

generate notifications for an alarm based on a presence of abnormalities in the clinical analysis; and transmit the notifications over a communication network to a client device, wherein the alarm activates a web interface to cause the alarm to display on the client device and to enable a connection from the client device to the computing device.

2. The smart monitoring system of claim 1 wherein the activity signals include utilization of appliances and motion in given rooms or areas.

3. The smart monitoring system of claim 1 wherein the computer device is further configured to interpret activities based on type and location of the plurality of sensor devices.

4. The smart monitoring system of claim 3 wherein the activities include walking, sleeping, eating, exercise, and bathroom activities.

5. The smart monitoring system of claim 1 wherein the current scoring of the individual comprises a total of current scores of the scoring components.

6. The smart monitoring system of claim 1 wherein the historic scoring includes a comparison of the scoring components with a historical set of scoring components associated with the individual.

7. The smart monitoring system of claim 1 wherein the peer scoring includes a comparison of the scoring components with scoring components of other individuals.

8. The smart monitoring system of claim 7 wherein the other individuals are selected from a subset of a population according to one or more of age, race, sex, and location.

9. The smart monitoring system of claim 1 wherein the quality of life score comprises a weighted average or sum of the scoring components of the current scoring, the historic scoring, and the peer scoring.

10. The smart monitoring system of claim 1 wherein the computing device further determines incidents of panic and decreases the quality of life score based on the incidents of panic.

11. The system of claim 1 wherein the computing device further determines trends associated with health and safety conditions from the activity signals.

12. The system of claim 11 wherein the trends include behaviors in eating, sleeping, mobility and hygiene.

13. The system of claim 1 wherein the plurality of sensor devices are attached to appliances and fixtures selected from the group consisting of a toilet, a door, a window, a refrigerator, a television remote, and a medicine cabinet.

14. The system of claim 13 wherein the computing device further:
receives activity signals from a sensor device coupled to a handle of the toilet; and
determines a flushing of the toilet based on the activity signals from the sensor device coupled to the handle of the toilet.

15. The system of claim 13 wherein the computing device further:
receives activity signals from a sensor device coupled to the door; and
determines an opening or closing of the door based on the activity signals from the sensor device coupled to the door.

16. The system of claim 13 wherein the computing device further:
receives activity signals from a sensor device coupled to the window; and
determines an opening or closing of the window based on the activity signals from the sensor device coupled to the window.

17. The system of claim 13 wherein the computing device further:
receives activity signals from a sensor device coupled to the refrigerator; and
determines an opening or closing of the refrigerator based on the activity signals from the sensor device coupled to the refrigerator.

18. The system of claim 13 wherein the computing device further:
receives activity signals from a sensor device coupled to the television remote; and
determines watching of a television based on the activity signals from the sensor device coupled to the television remote.

19. The system of claim 13 wherein the computing device further:
receives activity signals from a sensor device coupled to the medicine cabinet; and
determines an individual taking medicine based on the activity signals from the sensor device coupled to the medicine cabinet.

20. A method, in a smart monitoring system comprising a processor and a memory, for monitoring an individual, the method comprising:
receiving, by a computing device, activity signals from a plurality of sensor devices within a home or facility, the activity signals including signals from one or more wireless transmitter devices coupled to an individual indicating a presence of the individual, and sensor data comprising values representative of measurements of movement associated with the presence of the individual and indicating usage of given ones of appliances and fixtures, wherein the usage of the given ones of the appliances and fixtures includes a button press and a press duration that is representative of urgency unique to the given ones of the appliances and fixtures;
parsing, by the computing device, the activity signals into scoring components by correlating the sensor data from the plurality of sensor devices to the scoring components, the scoring components including a sleep score, a motion score, and an event score;
computing, by the computing device, a current scoring of the individual based on the scoring components;
comparing, by the computing device, the current scoring of the individual to historic scoring of the individual and peer scoring of the individual, the historic scoring and the peer scoring computed based on the scoring components;
generating, by the computing device, a quality of life score for the individual based on the current scoring and using the comparison as a baseline;
processing, by the computing device, a clinical analysis of the individual based on the quality of life score, the clinical analysis including graphical representations of the quality of life score, the scoring components, and a trend associated with the individual's health based on the event signals, the trend including the indication of usage of the given ones of the appliances and fixtures corresponding to the presence of the individual and a distinctive press duration that indicates an emergency;

generating, by the computing device, notifications for an alarm based on a presence of abnormalities in the clinical analysis; and transmitting, by the computing device, the notifications over a communication network to a client device, wherein the alarm activates a web interface to cause the alarm to display on the client device and to enable a connection from the client device to the computing device.

* * * * *